United States Patent [19]

Dailey et al.

[11] Patent Number: 4,962,660
[45] Date of Patent: Oct. 16, 1990

[54] APPARATUS FOR IMPACT TESTING FOR ELECTRIC GENERATOR STATOR WEDGE TIGHTNESS

[75] Inventors: George F. Dailey, Plum Borough; Mark W. Fischer, Pittsburgh, both of Pa.

[73] Assignee: Westinghouse Electric Corp., Pittsburgh, Pa.

[21] Appl. No.: 367,658

[22] Filed: Jun. 19, 1989

[51] Int. Cl.$^5$ ............................................. G01N 3/30
[52] U.S. Cl. ........................................ 73/12; 73/865.8
[58] Field of Search .................... 73/12, 572, 582, 574, 73/662, 865.8

[56] References Cited

U.S. PATENT DOCUMENTS

| | | |
|---|---|---|
| 4,422,320 | 12/1983 | Moorby et al. |
| 4,502,329 | 3/1985 | Fukunaga et al. |
| 4,534,206 | 8/1985 | Kiso et al. |
| 4,803,563 | 2/1989 | Dailey et al. |
| 4,811,091 | 3/1989 | Morrison et al. |

FOREIGN PATENT DOCUMENTS 0207013 10/1985 Japan .................................... 73/572

Primary Examiner—Charles A. Ruehl

[57] ABSTRACT

A low profile remotely controlled carriage which is inserted between the rotor and stator of an electric generator carries an impactor which can be preloaded to strike the stator wedges in all orientations around the stator with a selected high impact force which causes the stator wedge to vibrate. A detector seismically isolated from the impactor measures the deflections in the vibrating stator wedge. Preferably, the detector includes an eddy current coil positioned to measure the distance to a wedge follower which vibrates with the wedge. In one embodiment, the wedge follower is a vacuum cup secured to the wedge. In another, the eddy current coil measures the distance to a foot spring biased against the vibrating wedge. Preferably, the detector is seismically isolated by mounting it on a separate carriage disposed in an aperture in the low profile carriage.

29 Claims, 10 Drawing Sheets

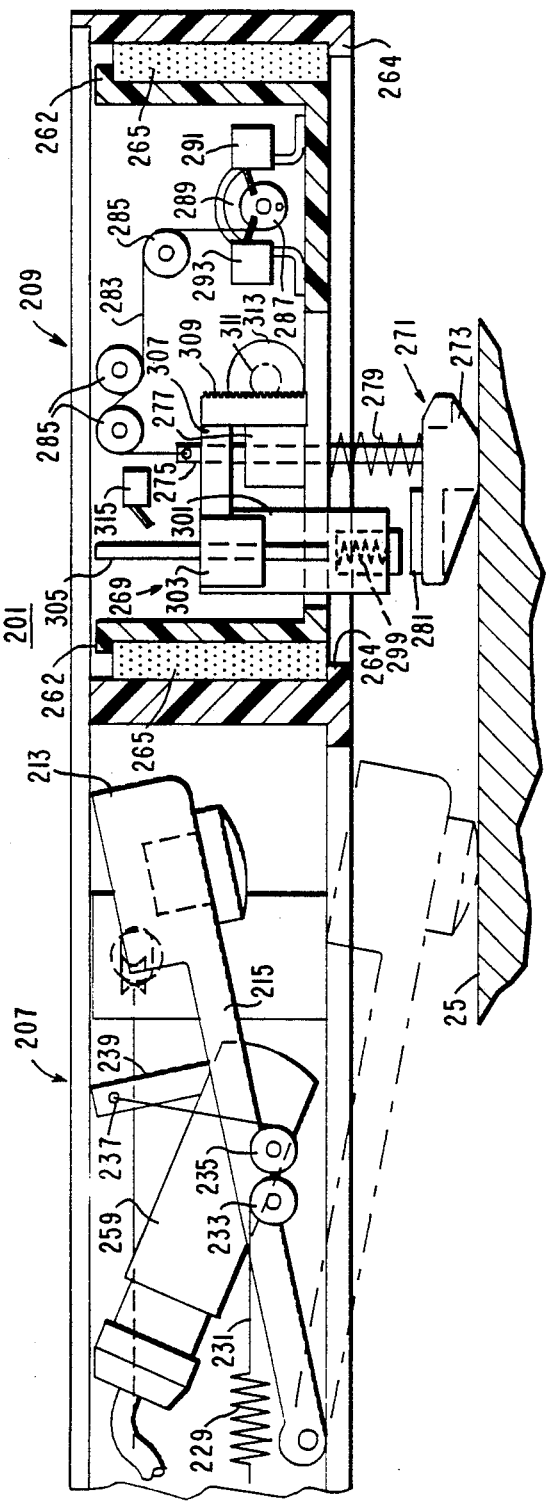

APPARATUS FOR IMPACT TESTING FOR ELECTRIC GENERATOR STATOR WEDGE TIGHTNESS

BACKGROUND OF THE INVENTION

1. Field of the Invention

This invention relates to apparatus for remotely testing electric generator stator wedge tightness with the rotor in place. More particularly, it relates to such apparatus which includes a remotely controlled carriage small enough to fit into the air gap between the generator rotor and stator, and carrying an impactor to induce vibration in the wedges which is measured by an eddy current device.

2. Background Information

During scheduled and some forced outages of electric utility steam driven electric generators, one of the major concerns is the condition of the stator coils. Many tests are performed to quantify stator integrity. The most time consuming of these tests has been the test of stator wedge tightness since it has required removal of the rotor to gain access to the stator bore area, specifically the tooth tip area where the wedges are located. Removal of the rotor requires two to three days alone. The accepted industry method of testing stator wedge tightness is for a technician to "tap" the wedge, feel the resulting vibration, and listen to the sound. A loose wedge will vibrate more than a tight one, and can be felt with the fingers. In addition, a loose wedge will emit a characteristic hollow sound, which the experienced technician quickly learns to recognize as a loose wedge.

It is very important that wedge tightness be carefully ascertained and corrected if deficient because the tightness of the stator wedge is the only structural element that prevents stator coil vibration due to the combined effects of magnetic and mechanical loading. Field experience has shown that failure to hold the stator coil stationary in the stator slot permits ever increasing levels of vibration leading to deterioration and finally failure of the stator mica insulation and, in many instances, grounding or "flashover" of the coils. When this occurs, the owner/operator of the unit is faced with a time-consuming and expensive rewinding process. For these reasons, stator wedge tightness is of interest during routine outages, and not just when the rotor is removed.

One of the difficulties in testing wedge tightness without removal of the rotor is that there is as little as 1½ inches of clearance between the stator bore and the retainer ring through which apparatus may be inserted to inspect the wedges distributed along the length of the stator. Another difficulty is that the wedges are made of non-conductive, non-magnetically permeable material such as, for example, fiberglass coated with Kevlar which is, compared to other materials such as steel, an absorbent of mechanical energy so that the techniques available for measuring tightness are limited. An additional difficulty, especially in the case of an impact tester, is that the stator coils extend radially outward about a horizontal axis such that the effect of gravity on the impactor varies with the angular position of the stator wedge being tested.

Commonly owned U.S. Patent Application Ser. No. 277,472 filed on Nov. 23, 1988, now U.S. Pat. No. 4,889,000 which is a continuation of parent application No. 013,478 filed on Feb. 11, 1987, now U.S. Pat. No. 4,733,750 discloses a low profile remotely controlled carriage for insertion into the gap between the rotor and stator of an electric generator for performing inspections. The carriage is positioned over a wedge with the aid of a miniaturized television camera. A solenoid when energized strikes the wedge and a microphone records the acoustic response. It has been found, however, that it is desirable to apply a larger and more repeatable impact force to the wedge than can be developed by a solenoid. It has also been found that it is difficult to assess with a computer the acoustic response recorded by the microphone.

The inspection apparatus of patent application Ser. No. 277,472 filed on Nov. 23, 1983 also includes an eddy current tester which is used to assess the condition of the insulation between stator laminations. Commonly owned U.S. patent application Ser. No. 4,803,563 also discloses an eddy current tester mounted on a carriage inserted between the rotor and stator of an electric generator for inspecting the insulation between the stator laminations. The carriage in U.S. Pat. No. 4,803,563 is held in place against the stator by permanent magnets embedded in the carriage chassis.

Other attempts have been made to quantify the "tap, listen and feel" process for testing stator wedge tightness. A mechanical impedance probe has been developed which is based upon the recognition that during a resonance sweep, a tight wedge will resonate (shift phase) at a slightly higher frequency than a loose one. This method does not discriminate between different degrees of looseness nor does the apparatus have sufficient power to resonate wedges of the size and style used with the larger steam driven units. In addition, the unit is too large to fit into the rotor stator air gap.

Another type of apparatus for measuring wedge tightness uses a force measurement system. The theory of operation is that when an impact force is applied to a stator wedge, the hammer will maintain contact with a loose wedge for a longer interval before recoiling than with the same wedge in a tight condition. This has been confirmed, however, the sensitivity of the test does not permit clear discrimination between the tight and loose conditions. Furthermore, a version of such a device small enough for use in the air gap of the generator has not been developed.

There is a need therefore for improved apparatus for determining generator stator wedge tightness.

There is also need for such a apparatus which can provide a more vigorous quantitative assessment of wedge tightness.

There is an associated need for such apparatus which can provide a consistent quantitative assessment through all the orientations required to test wedge tightness around the stator.

There is a further need for such apparatus which can determine wedge tightness without removal of the rotor.

BRIEF DESCRIPTION OF THE DRAWINGS

A full understanding of the invention can be gained from the following description of the preferred embodiments when read in conjunction with the accompanying drawings in which:

FIG. 10 is a vertical section in enlarged scale through part of the modified carriage shown in FIG. 9 taken along the line X—X.

DESCRIPTION OF THE PREFERRED EMBODIMENTS

Figure 1:
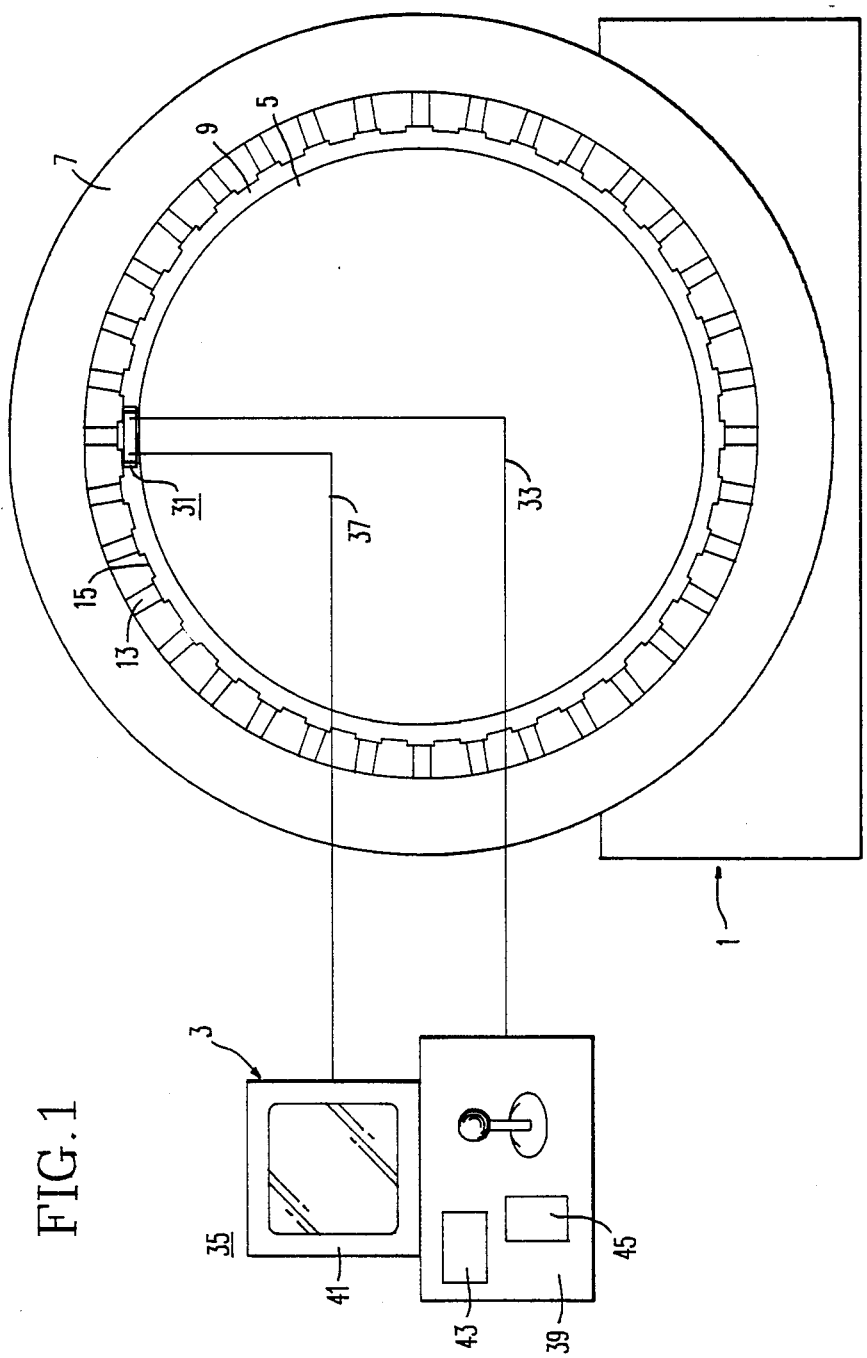
FIG. 1 is a schematic view of an electric generator with the inspection system of the invention in place to perform an inspection of generator stator wedge tightness.

FIG. 1 illustrates schematically a large steam turbine driven electric power generator 1 with the inspection system 3 of the invention in place for measuring generator stator wedge tightness. The generator 1 includes a rotor 5 mounted for rotation within a stator 7. A narrow gap 9 is formed between the rotor retainer ring 11 and the stator. In some electric generators, this gap 9 can be as narrow as one and half inches. The stator 7 includes stator coils 13 positioned between longitudinally extending stator teeth 15.

Figure 2:
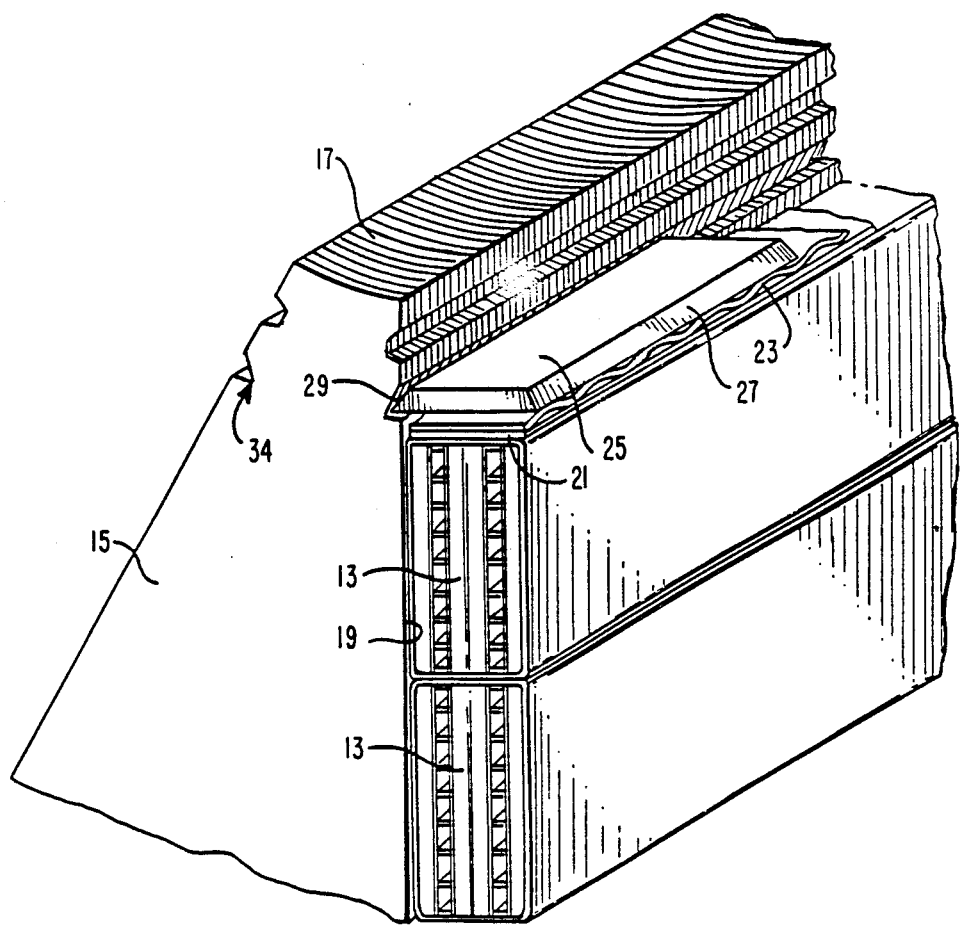
FIG. 2, is a fragmentary isometric view of a portion of the stator of the electric generator of FIG. 1 illustrating the manner in which the stator coil is held in place.

As shown more clearly in FIGS. 2, the stator teeth 15 which are made of laminations 17 form stator slots 19 in which stator coils 13 are stacked in pairs, one on top of the other. The stator coils 13 are retained in the slots 19 by shims 21, sections of ripple springs 23, and stator wedges 25 having beveled edges 27 which engage correspondingly shaped grooves 29 in the sidewalls of the stator teeth 15. The ripple spring sections 23 are compressed between the stator wedges and shims 21 to generate a force which firmly holds the coils in place. Over time, the ripple springs can lose their resiliency so that the wedges become loose. As previously mentioned, this permits the coils 13 to vibrate which can result in damage to the coil and eventual failure of the coil insulation. The present invention inspects stator wedge tightness so that corrective action can be taken before this occurs.

Returning to FIG. 1, the inspection system 3 of the invention includes a low profile main carriage 31 which is inserted in the narrow gap 9 between the rotor and stator and travels along the stator slot inspecting the wedges for tightness. As will be seen, the low profile main carriage 31 carries an impactor which sets up vibrations in the stator wedges and a detector which generates electric signals in response to those vibrations. The low profile carriage 31 also carries a miniature television camera which the operator can use to successively position the low profile main carriage over successive stator wedges in the slot and by which he can monitor operation of the impactor. Electrical signals to and from the low profile main carriage to control positioning of the carriage and operation of the impactor and the detector, and data signals from the detector are carried by an electrical cable 33 connected between the low profile main carriage 31 and a console 35. Similarly, control and video signals to and from the video camera are carried between the main carriage and the console by cable 37. The cable 33 is connected to an electronic control box 39 while the cable 37 carrying the video signals is connected to a monitor 41. The electronic control box 39 includes a display 43 and a key pad 45 through which the operator can interface with and control the inspection system. The monitor 41, permits the operator to position the main carriage 31 over a selected stator wedge and to observe operation of the impactor.

Figure 3:
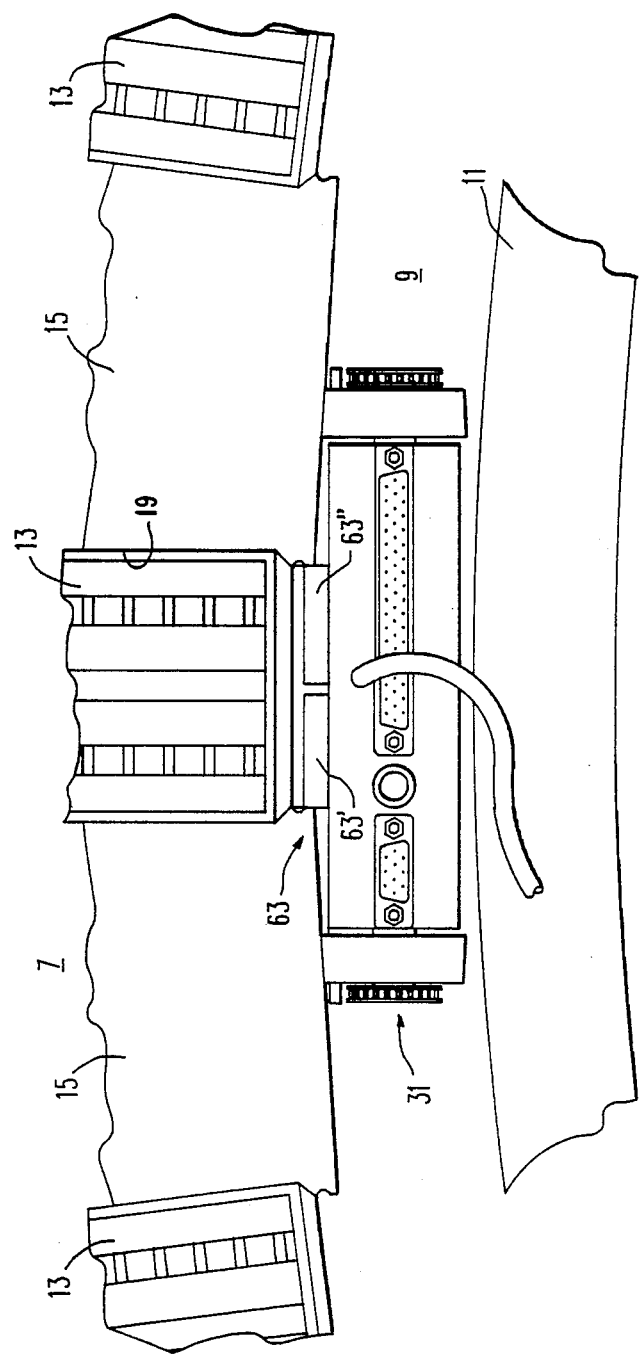
FIG. 3 is rear view of the low profile main carriage of the inspection system of the invention shown in place within the electric generator of FIG. 1.
Figure 4:
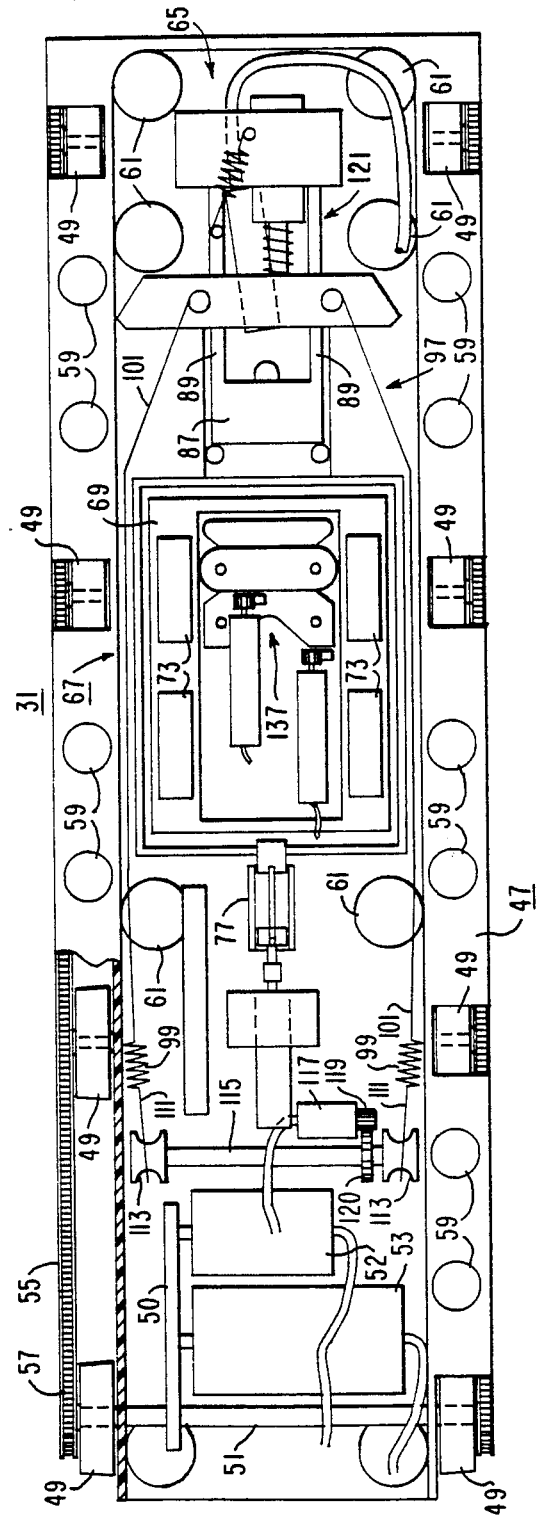
FIG. 4 is a top plan view of the low profile main carriage of the inspection system of the invention with the top cover removed.
Figure 5:
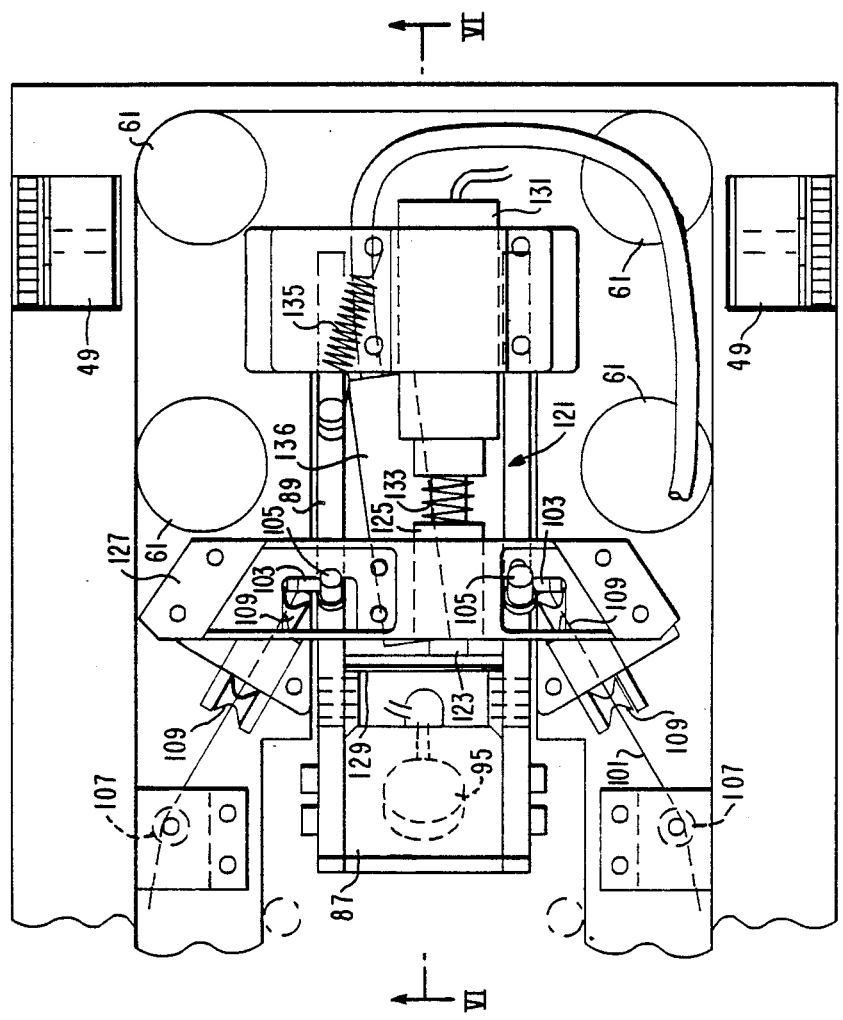
FIG. 5 is a view of a portion of FIG. 4 shown at an enlarged scale.

Referring especially to FIGS. 3 through 8, the low profile main carriage 31 has a chassis 47 made of a non-electrically conductive, non-magnetically permeable material such as fiberglass. Rotatably mounted along each side of the chassis 47 are four wheels 49. The rear wheels 49 are mounted on a shaft 51 which is driven through a timing belt 50 by an electric motor 53 mounted on the chassis 47. Chains 55 engage sprockets 57 to drive all of the drive wheels 49 with the motor 53. An encoder 52 also driven by timing belt 50 provides signals representing carriage movement to the electronic control box 39 for determining the position of the carriage. A number of one half inch diameter and one inch diameter neodymium magnets 59 and 61 respectively are distributed over the chassis 47. These magnets secure the main carriage to the stator for all locations of the stator slots around the interior of the stator. Guides 63 mounted on the bottom of the chassis 47 engage the stator slot 19 as seen in FIG. 3 to direct the main carriage along a selected slot. Parts 63' of the guides 63 are movable laterally with respect to a fixed part 63" to adjust the width of the guide to accommodate for variations in the width of the stator slots in different machines. As described to this point, the main carriage 31 is similar to that described in U.S. Pat. No. 4,803,563.

The main carriage 31 carries an impactor 65 and a vibration detector 67. The vibration detector 67 is mounted on a seismically isolated detector carriage 69 disposed in an aperture 71 in the chassis 47 of the main carriage 31. This detector carriage 69 is supported by four free-turning wheels 73 and has its own set of neodymium magnets 75 to secure it to the stator in all orientations. The detector carriage 69 is selectively coupled with the main carriage by a gripper 77 mounted on the chassis 47 by mounting 79. The gripper 77 has a pair of jaws 81 which are opened and closed by a motor 82 having a threaded shaft 83 journaled in support 88 and engaging a traveling nut 84 carrying a pair of actuating arms 85 pinned to the jaws 81. Gripper 77 positions the detector carriage 69 within the aperture 71 by gripping a rod 80 so that the detector carriage 69 is seismically isolated from the remainder of the main carriage by the gap 86 when the the jaws 81 are opened. This seismic isolation of the detector assures that the deflection measurements made by the detector are not magnified by the direct transmission of movement of the impactor through the main carriage.

The impactor 65 includes an impactor head 87 pivotally mounted by a pair of support arms 89 for movement along an arcuate path 91. A hemispherical nose 93 on the impactor head concentrates the force generated by the impactor which is measured by a force cell 95.

The impactor 65 must generate enough force to compress the ripple spring 23 beneath the stator wedge 25.

The tighter the wedge, the greater the force required to achieve this. It has been determined that energy in excess of one foot pound which generates a force at the point of impact of at least two hundred pounds is required for reliable wedge tightness measurement. While the impactor head 87 has a sizeable mass, the length of the stroke over which it can be accelerated is restricted by the width of the air gap between the stator and the rotor. Furthermore, gravity cannot be relied upon to accelerate the impactor head since the impactor must be able to operate in all orientations including up side down. The invention includes a mechanism 97 for applying a selected driving force to the impactor head.

The driving force mechanism 97 includes a pair helical tension springs 99 connected to the pivot arm 89 through cables 101 secured to pins 103 extending laterally from uprights 105 mounted on the pivot arms. The cables 101 are reeved around the detector carriage by pulleys 107 and directed upward to pins 103 by pulleys 109. It will be noted that the axes of the springs 99 lie in the plane of the main carriage 31 so that they may be extended the required length to generate the appropriate driving force for the impactor within the limited space available between the rotor and stator. Connected to the other end of each of the springs 99 is a cable 111 which is wound on a windless pulley 113. The windless pulleys 113 are mounted on a common shaft 115 driven by a motor 117 through pinion gear 119 and gear 120.

Figure 6:
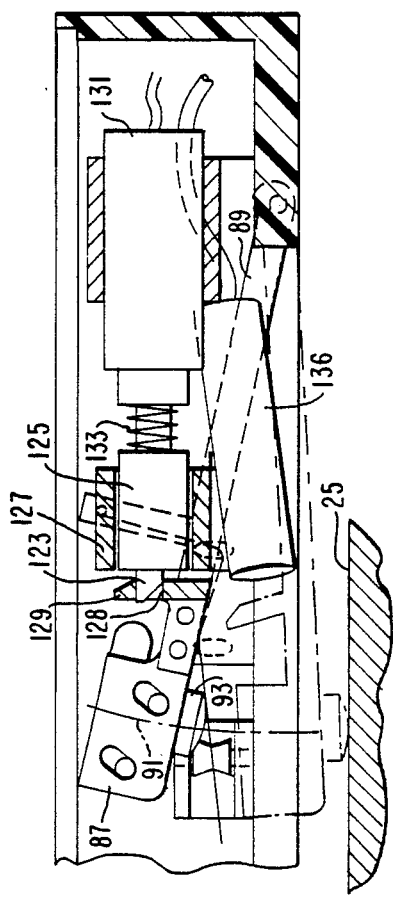
FIG. 6 is a vertical section through the portion of the low profile carriage shown in FIG. 5 taken along the line VI—VI.
Figure 7:
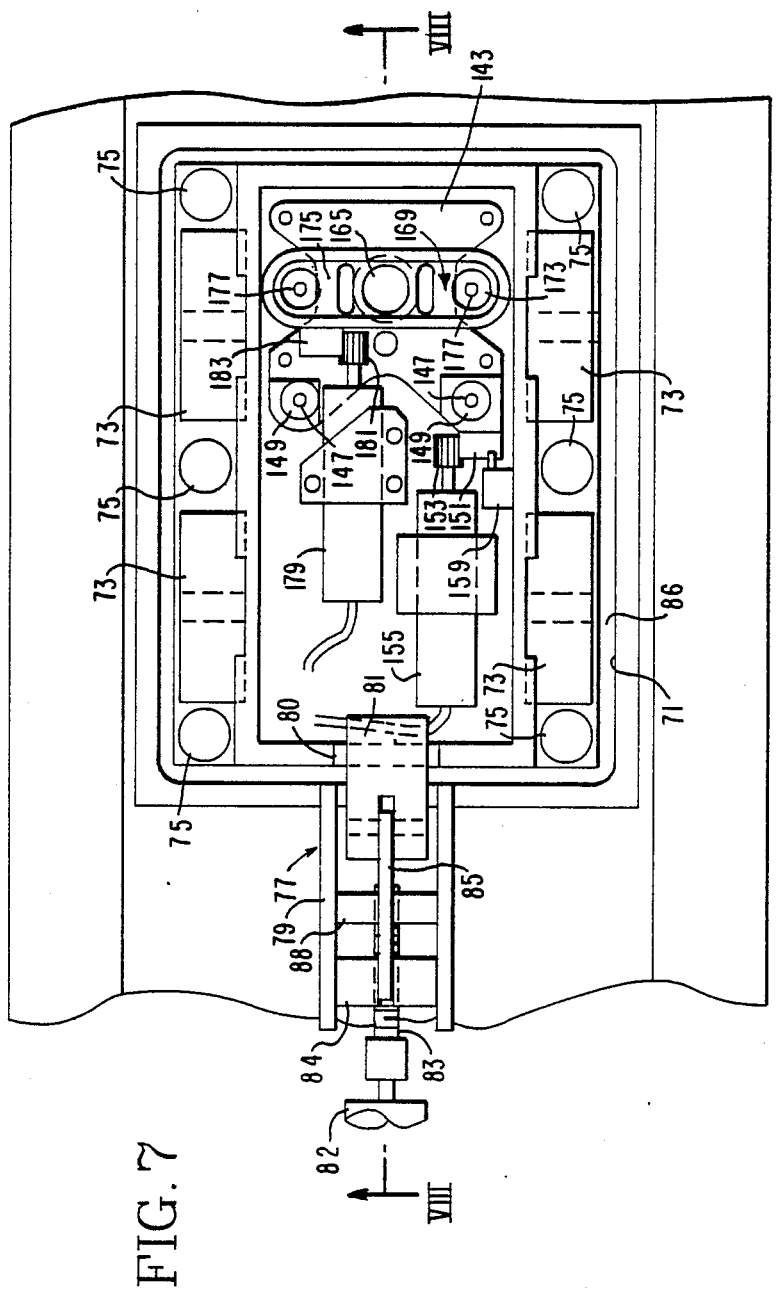
FIG. 7 is a plan view of the detector and gripper portions of the low profile carriage.
Figure 8:
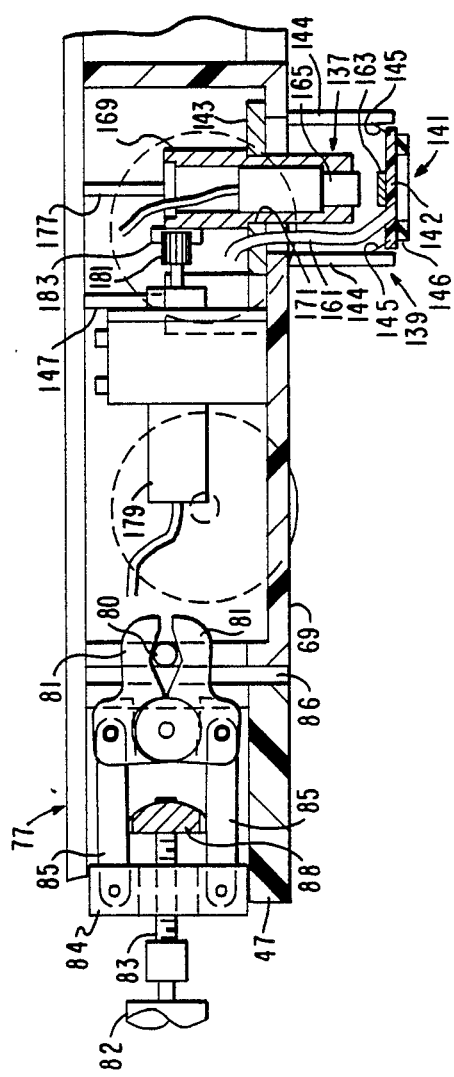
FIG. 8 is a vertical section of the detector and gripper taken along the line VIII—VIII in FIG. 7.

A latch mechanism 121 which retains the impact head in a cocked position shown in full line in FIG. 6 includes a latch pin 123 which slides in a Teflon resin bearing 125 supported by a support bracket 127 straddling the pivot arms 89. The latch pin 123 engages a notch 128 in a cross bar 129 spanning the pivot arms 89. The latch pin 123 is retracted by a pulsing dc solenoid 131. A spring 133 biases the latch pin 123 to the latched position. By control of the motor 117, appropriate tension can be applied to the springs 99 so that the impactor 65 generates a constant impact force for all orientations of the main carriage 31. A return spring 135 returns the impactor head 87 to the cocked position when tension on the springs 99 is relieved.

A miniature television camera 136 is mounted on the low profile carriage to provide the operator with a view of the impactor and detector for positioning the carriage and observing the test.

The vibration detector 67 mounted on the detector carriage 69 includes an eddy current detector 137. Since the stator wedges are electrically non-conducting, a wedge follower 139 which is at least in part electrically conducting is also provided. In the embodiment shown in FIGS. 7 and 8, the wedge follower is a vacuum cup 141. The vacuum cap 141 is suspended from a roughly X shaped mounting plate 143 with four depending support rods 144 by helical extension springs 145. The mounting plate 143 has a pair of upstanding shafts 147 which slide in linear bearings 149 mounted on the detector carriage 69. A rack 151 projecting from the mounting plate 143 is engaged by a pinion gear 153 on the shaft of a motor 155. Operation of the motor 155 raises and lowers the mounting plate 143 to selectively bring the vacuum cup 141 into contact with the adjacent stator wedge. In the extended position, a limit switch 159 turns on a vacuum pump (not shown) which evacuates the vacuum cup 141 through a vacuum hose 161 to securely attach the vacuum cup 141 to the adjacent stator wedge so that the vacuum cap 141 accurately follows deflection of the stator wedge resulting from the vibrations set up by the impactor 65. The vacuum cup 141 is a nylon disc 142 with a rubber ring 146 secured to its lower surface. To provide the electrically conductive material required for operation of the eddy current detector, a piece of copper foil 163 is attached to the vacuum cup 141.

The eddy current detector 137 comprises an eddy current coil 165 mounted in the base 167 of a generally T shaped sensor holder 169 which extends through a hole 171 in the mounting plate 143. Linear bearings 173 in the arms 175 of the T shaped sensor holder 169 ride on a pair of shafts 177 mounted on the detector carriage 69 so that the eddy current coil 165 can be raised and lowered to a fixed distance from the vacuum cup 141 by a motor 179 having a pinion gear 181 which engages a rack 183 secured to the sensor holder 169.

In operation, the low profile main carriage 31 is inserted through the gap 9 between the rotor 5 and stator 7 of the electric generator 1 with the guides 63 engaging the mouth of a selected stator slot 19. The magnets 59 and 61 hold the carriage 31 in place against the stator regardless of the position of the selected stator slot 19 around the stator. The drive motor 53 is then energized to drive the low profile main carriage 31 along the slot to position the carriage, as observed on the monitor 41, so that the impactor nose 87 will strike the so-called "sweet spot" or wedge centroid of a selected wedge while the vacuum cup 141 is positioned to monitor the vibration at the end of the wedge. Positioning the impactor in this manner produces maximum wedge vibration for a given impact.

With the impactor positioned at the desired spot over the selected wedge, the motor 83 is operated to open the clamp 77 and isolate the detector carriage 69 from the main carriage 31. The magnets 75 hold the detector carriage 69 in position against the stator. The motor 155 is then operated to extend the vacuum cup 141 into contact with the selected wedge and operation of limit switch 159 turns on the vacuum pump to apply a vacuum through vacuum line 161 to firmly secure the vacuum cup 141 to the selected wedge. Motor 179 is then operated in a fast mode to extend the eddy current coil 165 toward the piece of copper foil 163 secured to the vacuum cup 141. At a predetermined distance from the vacuum cup 141, the motor 179 is slowed down and the eddy current voltage is closely monitored for rapid decrease to zero which occurs at the pre-calibrated balance point, selected in the exemplary system to be 0.025 inches from the foil on the vacuum cup. At this point, the vacuum cup 141 and the eddy current coil 165 are correctly positioned and ready for measurement of a wedge impact.

In preparation for an impact, the impactor head is held in the cocked position by the latch pin 123. The motor 117 is operated to turn the windlass pulleys 113 to preload the tension springs 99 and thereby apply a driving force to the impactor head through cables 101. The motor 117 has an integral encoder which enables the control system to rotate the shaft of motor 117, and hence the windless pulleys 113, the correct number of turns. For example, when the impactor is operating "upside down" in the generator 12 o'clock position, the impactor is working against gravity and slightly more spring tension is required than in the 6 o'clock position. Adjusting spring tension for unit orientation assures consistent impact forces independent of unit orientation.

The wedge tightness test is performed by energizing the solenoid 131 to withdraw latch pin 123 from the cross bar 129 permitting the preloaded springs 99 to apply a driving force to the impactor head 87 causing the impactor head nose 93 to strike the stator wedge with the prescribed force. The resulting vibrations set up in the wedge are followed by the vacuum cup 141. The eddy current coil 165 generates a signal which is a function of the instantaneous spacing between the coil and the suction cup and therefore representative of wedge deflection. This arrangement measures wedge deflection with an accuracy which provides the capability of reliably distinguishing between the large amplitude vibrations of a loose wedge and the small amplitude vibrations of a tight wedge. The impactor is recocked for the next impact by return spring 135 when tension on the springs 99 is relieved.

Figure 9:
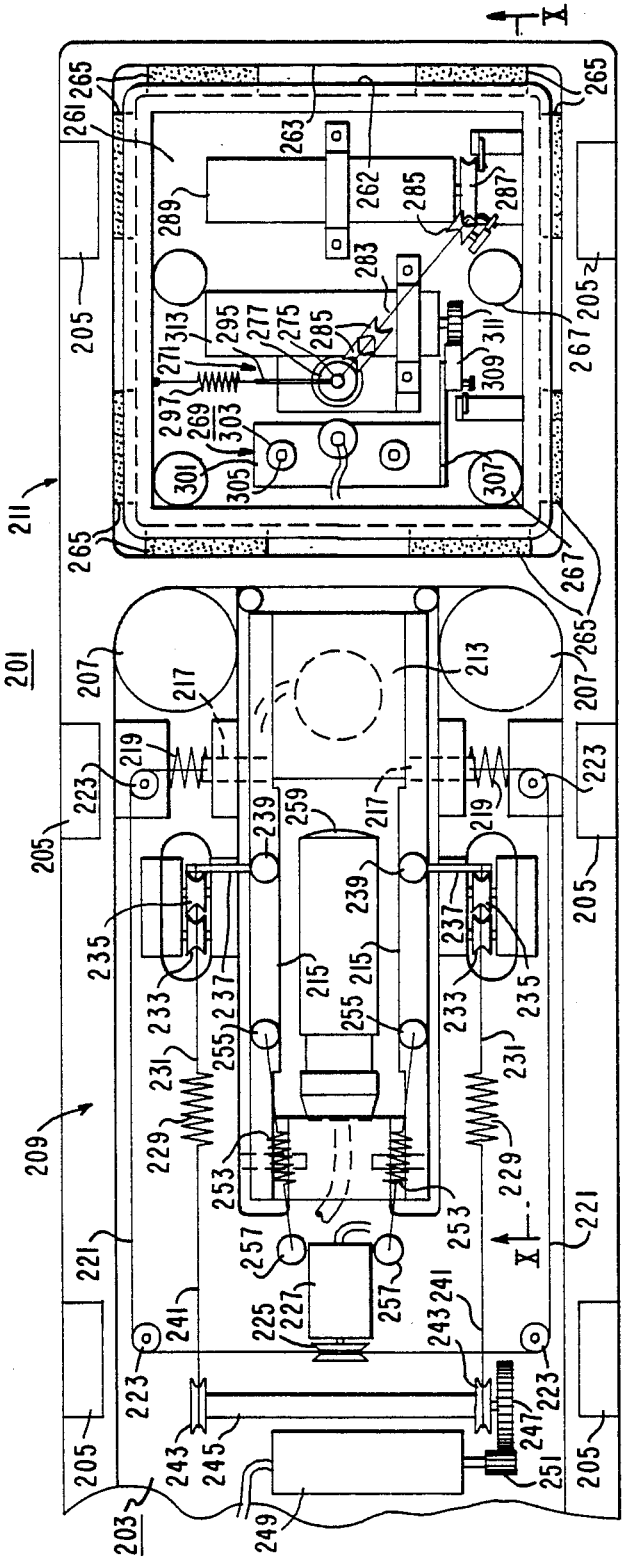
FIG. 9 top plan view of another embodiment of a low profile carriage in accordance with the invention.

FIGS. 9 and 10 illustrate an alternate embodiment of the invention. The modified carriage 201 has a chassis 203 which is constructed and driven by wheels 205, and is held in place against the stator by neodymium magnets 207, similarly to the carriage 31 previously described. Like the carriage 31, the modified carriage 201 mounts an impactor 209 and a detector 211. However, in this modified arrangement, the detector 211 is located at the end of the carriage 201 with the impactor 209 inboard. This permits the carriage to more easily test the last wedge in each stator slot.

Both the impactor 209 and detector 211 are modified from the corresponding mechanisms on the carriage 31. The impactor head 213 pivotally mounted by its support arms 215 is held in the cocked position by a pair of confronting latch pins 217 which are biased to the latched position by compression springs 219. The latch pins 217 are retracted by a pair of cables 221 which are reeved around pulleys 223 and wrapped in opposite directions around the windless pulley 225 on motor 227 mounted on the chassis 203. Preloading is applied to the impactor head in the cocked position by a pair of tension springs 229 connected to the impactor head 213 through cables 231 reeved over pulleys 233 and under pulleys 235 and connected to pins 237 extending laterally from posts 239 on the support arms 215. The other ends of the springs 229 are connected to cables 241 which are wound on windless pulleys 243. The windless pulleys 243 are mounted on a common shaft 245 having a gear 247 driven by a motor 249 through pinion 251. The impactor head 213 is biased to the cocked position by return springs 253 stretched between posts 255 on the support arms 215 and posts 257 mounted on the chassis. A miniature television camera 259 positioned between the support arms 215 of the impactor allows the operator to position the carriage 201 for testing of a selected stator wedge and to observe operation of the impactor and the detector.

The modified detector 211 includes a separate detector carriage 261 mounted in an aperture 263 in the chassis 203, but seismically isolated from the chassis 203 and supported by eight foam pads 265. The foam pads may be made for instance from low density closed cell urethane foam. Flanges 262 around the top of the detector carriage and 264 around the bottom of aperture 263 provide an interference fit with said foam pads to retain the detector carriage in said aperture. Separate neodymium magnets 267 secure the detector carriage 261 to the bore of the stator.

The carriage 261 carries an eddy current detector 269 and a wedge follower 271. The wedge follower 271 comprises a foot 273 mounted on the end of a shaft 275 which is journaled in a linear bearing 277 on the detector carriage 261. The foot 273 is biased against the stator wedge 25 by a helical compression spring 279. In order to maintain a low mass, the foot 273 is preferably made of a material such as nylon. Since such materials are non-conductive, a copper foil strip 281 is provided on the upper surface of the foot. While the carriage is being positioned over a stator wedge, the foot 273 is raised to a retracted position while the carriage is being positioned over a stator wedge by a cable 283 reeved over pulleys 285 and wound on a windless pulley 287 driven by a motor 289. Up and down limit switches 291 and 293 respectively, control the motor 289 to position the foot 273 in the extended and retracted positions. A rod 295 projecting laterally from the upper end of the shaft 275 is connected to the carriage 261 by a spring 297 to maintain the foot aligned with the eddy current detector.

The eddy current detector 269 includes an eddy current coil 299 mounted in eddy current coil housing 301. The housing 301 is supported for vertical movement by a pair of linear bearings 303 which ride on shafts 305 supported by the carriage 261. A bracket 307 attached to the eddy current coil housing 301 supports a rack 309 which engages a pinion gear 311 driven by a motor 313. Operation of the motor 313 raises and lowers the eddy current coil. A limit switch 315 sets the upper limit of travel. The coil 299 is lowered until the precise distance from the foil 281 on the foot 273 is reached at a preset null position as previously described.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. Apparatus for measuring the tightness of stator wedges in the stator of an electric generator without removing the rotor, said apparatus comprising:
   a low profile carriage insertable in a narrow gap between the rotor and stator and successively positionable adjacent selected stator wedges;
   an impactor carried by said low profile carriage, said impactor striking the selected stator wedge to set up a mechanical vibration therein; and
   a vibration detector mounted on said low profile carriage, said vibration detector comprising:
   a wedge follower which bears against and follows said selected stator wedge as said wedge vibrates in response to being struck by said impactor, said wedge follower being at least in part electrically conductive; and
   an eddy current coil positionable at a stationary point spaced from said wedge follower generating an electrical signal which varies with changes in spacing between the wedge follower and the eddy current coil as said wedge follower vibrates with said selected stator wedge.

2. The apparatus of claim 1 wherein said wedge follower comprises:
   a vacuum cup secured to said selected stator wedge by vacuum;
   means applying a vacuum to said vacuum cup; and an electrically conductive member secured to said vacuum cup.

3. The apparatus of claim 1 wherein said wedge follower comprises:
a foot member; and
spring bias means biasing said foot member into contact with said selected stator wedge.

4. The apparatus of claim 1 including means extending said wedge follower into and out of contact with said selected stator wedge.

5. The apparatus of claim 4 including means extending said eddy current coil from a retracted position to said stationary point spaced from the wedge follower when the wedge follower is extended into contact with said selected stator wedge.

6. The apparatus of claim 1 including means seismically isolating said vibration detector from said impactor.

7. The apparatus of claim 6 wherein said means seismically isolating said vibration detector comprises;
a separate detector carriage on which said vibration detector is mounted; and
means selectively coupling and decoupling said separate detector carriage from said low profile carriage.

8. The apparatus of claim 7 wherein said low profile carriage defines an aperture therethrough and wherein said detector carriage is disposed in said aperture in said low profile carriage with spacing between the detector carriage and the low profile carriage.

9. The apparatus of claim 6 wherein said means seismically isolating said vibration detector comprises:
a separate detector carriage on which said vibration detector is mounted, said low profile carriage defining an aperture therethrough in which said detector carriage is disposed; and
vibration absorbing means connecting said detector carriage to said low profile carriage.

10. The apparatus of claim 1 wherein said impactor comprises:
an impactor head;
mounting means mounting said impactor head for movement along a predetermined path toward the selected stator wedge;
means applying a selected driving force to said impact head driving said impact head along said predetermined path to strike the selected stator wedge; and
latch means restraining said impactor head in a cocked position spaced from the selected stator wedge against said driving force and releasing said impactor head to be driven along said predetermined path by said driving force when unlatched.

11. The apparatus of claim 10 wherein said means applying said selected driving force to said impactor head comprises:
spring means connected to said impactor head; and
means preloading said spring means to a selected preload.

12. The apparatus of claim 11 wherein said low profile carriage is generally planar and defines a plane extending parallel to planes defined by said stator wedges, wherein said predetermined path along which said impactor moves is transverse to said plane defined by said low profile carriage, and wherein said spring means includes at least one spring having an axis extending in said plane of said carriage, and cable means applying a force produced by said at least one spring to said impactor head to drive said impactor head along said predetermined path.

13. The apparatus of claim 12 wherein said cable means is connected to one end of said at least one spring, and wherein said means preloading said at least one spring comprises motor driven means selectively applying a preloading force to the other end of said at least one spring.

14. Apparatus for measuring the tightness of stator wedges in the stator of an electric generator without removing the rotor, said apparatus comprising:
a low profile remotely controlled carriage insertable in a narrow gap between the rotor and stator and successively positionable adjacent selected stator wedges;
an impactor carried by said low profile carriage, said impactor striking the selected stator wedge to set up a mechanical vibration therein;
a vibration detector carried by said low profile carriage detecting deflection of the selected stator wedge as said wedge vibrates in response to being struck by said impactor; and
means seismically isolating said vibration detector from said impactor.

15. The apparatus of claim 14 wherein said vibration detector comprises:
a wedge follower which bears against and follows said selected stator wedge as said wedge vibrates in response to being struck by said impactor, said wedge follower being at least in part electrically conductive; and
an eddy current coil positionable at a stationary point spaced from said wedge follower generating an electrical signal which varies with changes in spacing between the wedge follower and the eddy current coil as said wedge follower vibrates with said selected stator wedge.

16. The apparatus of claim 15 including means extending said wedge follower into and out of contact with said selected stator wedge.

17. The apparatus of claim 16 wherein said wedge follower comprises:
a vacuum cup secured to said selected stator wedge by vacuum;
means applying a vacuum to said vacuum cup; and
an electrically conductive member secured to said vacuum cup.

18. The apparatus of claim 16 wherein said wedge follower comprises:
a foot member; and
spring bias means biasing said foot member into contact with said selected stator wedge.

19. The apparatus of claim 14 wherein said seismically isolating means comprises a separate detector carriage carrying said vibration detector and means selectively coupling and decoupling said separate detector carriage from said low profile carriage.

20. The apparatus of claim 19 wherein said low profile carriage defines an aperture therethrough and wherein said separate detector carriage is disposed within said aperture in said low profile carriage.

21. The apparatus of claim 20 wherein said means selectively coupling and decoupling said separate detector carriage from said low profile carriage comprises means positioning said separate detector carriage within said aperture in said low profile carriage with a space between the low profile carriage and the separate detector carrier.

22. The apparatus of claim 21 wherein said positioning means comprises a releasable clamp for selectively clamping said separate detector carriage at a position in said aperture in the low profile carriage with said annular space between said low profile carriage and the separate detector carriage.

23. The apparatus of claim 22 wherein said vibration detector comprises:
 a wedge follower which bears against and follows said selected stator wedge as said wedge vibrates in response to being struck by said impactor, said wedge follower being at least in part electrically conductive; and
 an eddy current coil positionable at a stationary point spaced from said wedge follower generating an electrical signal which varies with changes in spacing between the wedge follower and the eddy current coil as said wedge follower vibrates with said selected stator wedge.

24. The apparatus of claim 23 including means extending said wedge follower into and out of contact with said selected stator wedge.

25. The apparatus of claim 14 wherein said means seismically isolating said vibration detector comprises:
 a separate detector carriage on which said vibration detector is mounted, said low profile carriage defining an aperture therethrough in which said detector carriage is disposed; and
 vibration absorbing means connecting said detector carriage to said low profile carriage.

26. The apparatus of claim 25 wherein said aperture in said low profile carriage is adjacent and end of said low profile carriage.

27. Apparatus for measuring the tightness of stator wedges retaining stator coils in stator slots distributed around the interior of a horizontally oriented electric generator stator without removing the generator rotor, said apparatus comprising:
 a low profile carriage insertable in a narrow gap between the rotor and stator and successively positionable adjacent selected stator wedges in selected stator slots;
 an impactor carried by said low profile carriage and having an impactor head which strikes said selected stator wedge setting up a mechanical vibration therein, and means applying to said impactor head a driving force adjusted for the effect of gravity on the impactor head such that said impactor head strikes the selected stator wedge with a selected force at all stator slots around said horizontally oriented stator; and
 a vibration detector carried by said low profile carriage detecting deflection of the selected stator wedge as said wedge vibrates in response to being struck by said impactor head with said selected force.

28. The apparatus of claim 27 wherein said means applying said driving force to said impactor head comprises: spring means connected to said impactor head, means preloading said spring means to said adjusted driving force, and latch means restraining said impactor head in a cocked position spaced from the selected stator wedge against said adjusted driving force and releasing said impactor head to be driven by said adjusted driving force toward said selected stator wedge when unlatched.

29. The apparatus of claim 28 including means measuring the impact force with which said impactor head strikes said selected stator wedge.

* * * * *